| United States Patent [19] | [11] | 4,349,481 |
|---|---|---|
| Lischewski et al. | [45] | Sep. 14, 1982 |

[54] TRITIATED GIBBERELLIN ALDEHYDES

[75] Inventors: Manfred Lischewski, Halle-Neustadt; Habil G. Adam, Halle, both of German Democratic Rep.; Edward P. Serebryakov, Moskav, U.S.S.R.

[73] Assignee: Akademie der Wissenschaften der DDR, Berlin, German Democratic Rep.

[21] Appl. No.: 24,780

[22] Filed: Oct. 15, 1979

[30] Foreign Application Priority Data

Apr. 13, 1978 [DD] German Democratic Rep. ... 204770

[51] Int. Cl.³ .............................................. C07D 307/00
[52] U.S. Cl. ...................................... 549/297; 71/89; 204/158 R
[58] Field of Search ................................ 260/343.3 G

[56] References Cited

FOREIGN PATENT DOCUMENTS 112753 5/1975 Fed. Rep. of Germany.
120875 7/1976 Fed. Rep. of Germany.

OTHER PUBLICATIONS

Bearder et al., Phytochemistry, 1973, vol. 12, pp. 2173–2179 and 2655–2659.
Graebe et al., J.C.S. Chem. Comm. p. 161, 1975.
Hedden et al., J.C.S., Perkin I, pp. 587–592.
Lischewski et al., Tetrahedron Letters, No. 33, pp. 2835–2836, 1974, and No. 43, pp. 3691–3692, 1975 and No. 30, pp. 2569–2570.
Hanson et al., Phytochemistry, 1973, vol. 12, pp. 1073–1075.

*Primary Examiner*—Henry R. Jiles
*Assistant Examiner*—Jane T. Fan
*Attorney, Agent, or Firm*—Michael J. Striker

[57] ABSTRACT

Is the objective of the invention to develop a process for the production of tagged gibberellin-(7)-aldehydes which is of general applicability. As per the invention a gibberellin-(7)-aldehyde is converted into the gibberellin-(7)-aldehyde tagged at the C-15 position of the basic gibberellin skeleton under the influences of ultraviolet radiation, in given cases after the isolation of a developing 7-Hydroxy-7,15-cyclo butane derivative, and in the presence of compounds with tritium or deuterium donor properties respectively. The process is of particular suitability for the tagging of alkali-sensitive gibberellin-(7)-aldehydes. The tagged gibberellin-(7)-aldehydes produced by the process as per invention, are of importance for instance as primary materials for the obtaining of tagged natural gibberellins and their derivatives.

13 Claims, No Drawings

TRITIATED GIBBERELLIN ALDEHYDES

The invention concerns tagged gibberellin-(7)-aldehydes and a process for their production. Gibberellin-(7)-aldehydes are to be understood as gibberellin derivatives which have an aldehyde group in position 6 of the ent-gibberellan basic skeleton. Herein, the basic structure of ent-gibberellan is intact or only slightly modified (f.i. seco-, homo-, or nor-ent-gibberellan containing in a given instance also multiple bonds), and, in given instances, substituted in the most different ways. Tagged gibberellin-(7)-aldehydes are defined as such compounds which are tritiated or deuterated.

FIELD OF APPLICATION OF THE INVENTION

As phytohormones with multiple activity, gibberellins command great biological interest. Of particular importance is the application of tagged gibberellins and their derivatives in many fields, f.i. for bio-technical and analytical processes, for investigations of biosynthesis, metabolism, transportation, distribution, effects and structure-activity interaction of this group of phytohormones and their partially synthetic analogues as basis for the synthesis of new active media.

CHARACTERISTICS OF KNOWN TECHNICAL SOLUTIONS

Some tagged gibberellin-(7)-aldehydes have already been described. The preparation of [6-$^3$H-] respectively [6-$^2$H]-tagged gibberellin-A$_{12}$-aldehyde and gibberellin-A$_{14}$-aldehyde is reported by [J. R. BEARDER, J. MacMILLAN and B. O. PHINNEY, Phytochemistry 12, 2173, 2615 (1973); J. H. GRAEBE, P. HEDDEN and J. MacMILLAN, J. chem. Soc. Chem. Commun. 1975, 161; P. HEDDEN, J. MacMILLAN and B. O. PHINNEY, J. chem. Soc., Perkin I 1974, 587]. This process is, however, not of general application. In particular, alkali-sensitive gibberellin-(7)-aldehydes as f.i. gibberellin-A$_3$-(7)-aldehyde or gibberellin-A$_7$-(7)-aldehyde, cannot be produced by this method.

OBJECTIVE OF THE INVENTION

It is the objective of the invention to make available tagged gibberellin-(7)-aldehydes and to develop a generally applicable process for their production. In particular, this process should also be suitable for the tagging of alkali-sensitive gibberellin-(7)-aldehydes.

EXPLANATION OF THE NATURE OF THE INVENTION

The task of the invention consists in making available tagged gibberellin-(7)-aldehydes which are tritiated or deuterated to such a C-H bond which is present in unsubstituted form in nearly all gibberellin-(7)-aldehydes derived from natural gibberellins or their derivatives. The method of production should allow tagging at one carbon atom of the basic skeleton of ent-gibberellan, under such conditions of reaction wherein the alkali-sensitive characteristics of the skeleton will not be changed, this in order to ensure a wide band of application.

According to the invention, gibberellin-(7)-aldehydes are tagged at the C-15 position of the ent-gibberellan basic skeleton.

In the process as per invention, a gibberellin-(7)-aldehyde is converted to the gibberellin-(7)-aldehyde tagged at the C-15 position of the ent-gibberellan skeleton, which ensues under the influence of ultraviolet rays, in the presence of compounds with tritium or deuterium donor properties, (hereunder called: tritium or deuterium donors respectively), and, in given instances, after the isolation of a then developing 7-Hydroxy-7, 15-cyclobutane derivative.

The process according to the invention can be realized as a one-step or two-step process respectively. In the one-step process a gibberellin-(7)-aldehyde is converted into tagged gibberellin-(7)-aldehyde in the presence of tritium or deuterium donors respectively, and under the influence of ultraviolet light. In the two-step process, however, an untagged 7-Hydroxy-7, 15-cyclobutane derivative resulting during the photochemical conversion, is isolated as intermediate product, which, in the second step, and in the presence of tritium or deuterium donors respectively, is split to a tagged gibberellin-(7)-aldehyde.

The gibberellin-(7)-aldehyde used as primary materials were prepared chemically according to known processes [M. LISCHEWSKI and G. ADAM, GDR-Letters Pat. No. 112 753, C 07 d, 5/06; GDR-Letters Pat. No. 120 875, C 07 D, 307/77; M. LISCHEWSKI and G. ADAM, Tetrahedron Letters 1974, 2835; ibid. 1975, 2569; ibid. 1975, 3691; Z. Chem. 16, 486 (1976)] or microbially according to [J. R. BEARDER, J. MacMILLAN and B. O. PHINNEY, Phytochemistry 12, 2173 (1973); J. R. HANSON and J. HAWKER, J. chem. Soc., Chem. Comm. 1971, 208 and Phytochemistry 12, 1073 (1973)].

The photochemical conversion under the influence of ultraviolet rays is performed either in a solvent, f.i. in benzene, toluene methyl acetate, ethyl acetate, tetrahydrofuran, dioxane, methylene chloride, methanol, tert. Butanol or water, or respectively in a solvent mixture, f.i. in benzene/methylacetate, or in an aqueous or organic suspension, or work can proceed without a solvent wherein the primary materials can be used in crystalline or non-crystalline form, f.i. as a film or absorbed on an inorganic or organic carrier. Aluminum oxide, silica gel, florisil, celite, cellulose or organic polymers could, f.i., be used as carrier.

The most variegated substances containing exchangeable tritium or deuterium respectively, are suitable as tritium or deuterium donors. Tritium donors of particular advantage are for instance $^3$H$_2$O, XO-$^3$H and XS-$^3$H, wherein X stands for an alkyl, aryl, or acyl grouping which is substituted or unsubstituted.

An analogy prevails for deuterium donors. The following remarks on marking with tritium apply in a corresponding manner also to deuteration.

In order to attain a high specific radioactivity or a high rate of insertion respectively, the application of $^3$H$_2$O or CH$_3$O-$^3$H will be suitable. For the same reason, it is also of advantage to substitute all exchangeable hydrogen atoms in the gibberellin derivatives in order to have the total specific radioactivity of the tritium donors become specifically effective for the tagging at the C-15 position. From this it can be concluded that the process as per invention allows tritium tags that extend up to the specific radioactivity of carrier-free tritium. This is accomplished either by the application of substituted gibberellin-(7)-aldehydes or by the substitution of exchangeable hydrogen atoms on the level of the 7-Hydroxy-7, 15-cyclobutane derivative. It is, for instance, favorable to replace the hydrogen of the 7-hydroxyl group by a protective group before the splitting of the 7-Hydroxy-7, 15-cyclobutane derivatives. As protective group, an acyl group is preferably used, f.i. the acetyl, propionyl, butyril, benzoyl, or a substituted benzoyl group or, respectively, a silyl group, particularly the trimethylsilyl group or the tetrahydropyranil group.

The splitting of the 7-Hydroxy-7, 15 cyclobutane derivative, in a given case after the substitution of the hydrogen of the 7-hydroxyl group by a protective group, in the presence of a tritium or deuterium donor respectively, is effected by the addition of a base. Bases of the most varying nature can be used, for instance $OR^-$ or $SR^-$, wherein R stands for H, $^3$H or $^2$H respectively, an alkyl, or substituted alkyl, an aryl or substituted aryl, nitrogen-bearing bases, carbanions, hydride ions or basic ion exchangers. Conversion of 7-Hydroxy-7, 15-cyclobutane derivatives or the 7-acyloxy-7, 15-cyclobutane derivatives respectively can generally be accomplished directly already with catalytic amounts of bases, which is of particular importance with base-sensitive compounds.

The compound with tritium-donor properties can simultaneously be used with advantage as solvent, in a given case already for the photochemical conversion, and, in deprotonated form, as a base for splitting.

Temperature is playing a subordinate role in the photochemical conversion to 7-Hydroxy-7, 15-cyclobutane derivative and also in the fission, and it can be varied through a very wide range. The photochemical reaction can be effected at $-60°$ C. just as at $+50°$ C., and the quoted temperatures are by no means the limits of the temperature range within which the reaction will proceed successfully. The same applies to the splitting to a tagged gibberellin-(7)-aldehyde.

The concluding treatment of the products of reaction is made by the customary methods, for instance by column chromatography using organic solvents.

The process as per invention is of general applicability. Structural characteristics of alkaline sensitivity will not be changed. Tagging at the C-15 position is possible with nearly all gibberellin-(7)-aldehydes stemming from natural gibberellines and their derivatives. In this way, access is given to marked gibberellin-(7)-aldehydes that could hitherto not be produced in other ways. The process as per invention is also suitable for the preparation of double-tagged gibberellin-(7)-aldehydes. This process allows obtaining of [17-$^{14}$C, 15-$^3$H]-gibberellin-A$_3$-(7)-aldehyde from [17-$^{14}$C]-gibberellin-A$_3$-(7)-aldehyde and [1-$^3$H, 15-$^3$H]-gibberellin-A$_5$-(7)-aldehyde from [1-$^3$H]-gibberellin-A$_5$-(7)-aldehyde. Substituted gibberelline derivatives can also be prepared, as f.i. [$^{14}$C-glucose]-O(3)-B-D-glucopyranosyl-[15-$^3$H]-gibberellin-A$_3$-(7)-aldehyde from [$^{14}$C-glucose]-O(3)-B-D-glucopyranosyl-gibberellin-A$_3$-(7)-aldehyde.

The tagged gibberellin-(7)-aldehydes produced as per invention are of significance as primary materials for the obtaining of tagged natural gibberellins and their derivatives. The tag is located at a position at which biochemical changes, f.i. during studies of biosynthesis or investigations in regard of metabolism, are rarely observed. Further advantages are the stable tag, attainable with a high specific radioactivity, and the ease of proving.

The 7-Hydroxy-7, 15-cyclobutane derivatives or their acetylated substitutes respectively, appearing as intermediate products, represent a new group of phytohormone analogues, possessing modified growth-regulating activities.

The following examples will explain the invention, wherein, however, the special conditions as noted are not restricting the invention and can also be applied in the production of other compounds.

EXAMPLES OF REALIZATION

Example 1

330.4 mg (1 mMol) gibberellin-A$_3$-(7)-aldehyde (Ia) are dissolved in 15 ml abs. of benzene and 15 ml of methyl acetate and contained under argon in a quartz flask where they will be irradiated for 19 hours by a high-pressure mercury burner (THU 500 of Messrs. THELTA Electric Apparatus, Zella-Mehlis) located at a distance of 6 cm, with simultaneous cooling by a hair-drier-type blower. Thereafter the solution is concentrated under a vacuum and the residue is chromatographed on 20 g silica gel (Woelm). Elution with chloroform/ethyl acetate 8:2 vol/vol will produce 63 mg of unreacted gibberellin-A$_3$-(7)-aldehyde (Ia). Subsequently, 217 mg, 81% of theoretical value, of ent-3α, 7ξ, 10-13-tetrahydroxy-7, 15-cyclo-20-nor-gibberella-1, 16-diene-19-acid-19, 10-lactone (Ib) are obtained with chloroform/ethyl acetate 1:1 vol/vol. (Yield relative to converted Ia). The amorphous isomer mixture has the following spectroscopic data: IR (Nujol): $\nu_{max}$3400 (br.) and 1755 (γ-lactone-CO); MS: m/e 330 (M+).

217 mg of Ib are combined at room temperature with 10 ml of a sodium methylate solution (prepared from 10 ml CH$_3$O$^3$H and 15 mg Na; spec. radioactivity of CH$_3$O$^3$H=0.5 mCi/mMol). After 10 minutes, 1 ml of glacial acetic acid is added and concentration is made under vacuum. Subsequent chromatographic purification on 15 g silica gel (Woelm) will yield with chloroform/ethyl acetate 8:2 vol/vol, 134.5 mg (62% of theory) of [15-$^3$H]-gibberellin-A$_3$-(7)-aldehyde(Ic): amorphous; $[\alpha]_D^{25}$+119.2° (c=0.58, ethanol); IR (CHCL$_3$): $\nu_{max}$ 3610 (OH), 2820, 2725 and 1725 (aldehyde), 1775 (γ-lactone-CO), 1665 (=CH$_2$) and 1635 cm$^{-1}$ (—CH=CH—); MS: m/e 330 (M+); 100 MHz-NMR: $\nu_{TMS}^{COCl_3}$ 1.20 (s, 18-H$_3$), 2.79 (dd, J=10.5 and J'=2.5 Hz, 6-H), 3.22 (d, J=10.5 Hz, 5-H), 4.17 (d, J=3.5 Hz, 3-H), 5.00 and 5.29 (m, 17-H$_2$), 5.91 (dd, J=9.5 and J'=3.5 Hz, 2-H), 6.33 (d, J=9.5 Hz, 1-H) and 9.81 ppm (d, J=2.5 Hz, 7-H). The specific radioactivity is 0.43 mCi/mMol.

EXAMPLE 2

A solution of 414.5 mg (1 mMol) O(3), O(13)-diacetyl-gibberellin-A$_3$-(7)-aldehyde (IIa) in 40 ml abs. of benzene, in a quartz flask under nitrogen, and cooling by a hair-drier-type blower, is irradiated for 25 hours (THU of Messrs. THELTA Electro Apparatus, Zella-Mehlis). Thereafter, concentration is made under vacuum and the residue is chromatographed on 30 g silica gel (Woelm). The fractions 24–28 with a n-hexane/-chloroform gradient of 3:7 vol/vol will yield a return of 80 mg O(3), O(13)-diacetyl-gibberellin-A$_3$-(7)-aldehyde (IIa). With the same gradient, a combining of the fractions 30–55 will yield 305 mg $\triangleq$ 91% of theory, of ent-3α, 13-diacetoxy-7, 10-dihydroxy-7, 15-cyclo-20-nor-gibberellin 1.16-diene-19-acid-19, 10-lactone (IIb) (Yield relative to converted IIa).

The 7β Epimer of IIb can be isolated in pure state by multiple recrystallization from chloroform/n-hexane. The physical and spectroscopic data of ent-3α, 13-diacetoxy-7β, 10-dihydroxy-7, 15-cyclo-20-norgibberellin 1, 16-diene-19-acid-19, 10-lactone are: mp 217°–220°

C., (needles from chloroform/n-hexane); $[d]_D^{25} + 122.2°$ (c=0.45, ethanol); MS: m/e 414, (M+ f.i. M—); IR (CHCl$_3$): $\nu_{max}$ 3610 (OH), 1778 ($\gamma$-lactone-CO), 1740 (ester-CO), 1668 (>C=CH$_2$) and 1260 cm$^{-1}$ (acetyl); 100 MHz-NMR-spectrum: $\delta_{TMS}^{CDCl_3}$: 1.30 (s, 18-H$_3$), 2, 10 and 2.14 two acetyls, 3.03 (d, J=7 Hz, 5-H), 4.68 (inexact double J=7 Hz, 7-H), 4.86 (d, J=2.25 Hz, 17-H), 5.24 (d, J=2.75 Hz, 17-H), 5.36 (d, J=3.5 Hz, 3-H), 5.87 (dd, J=9.5 Hz and J'=3.5 Hz, 2-H), 6.41 (d, J=9.5 Hz, 1-H).

Analogous photochemical conversions of O(3-),O(13)-diacetylgibberellin-A$_3$-(7)-aldehyde (IIa) were also carried out in other solvents such as f.i. toluene, ethyl acetate, tetrahydrofuran, dioxane, methylen chloride, methanol, tert. butanol. The yields attained from 7-Hydroxy-7, 15-cyclobutane-derivative IIb relative to the converted aldehyde compound are between 80% and 92%.

0.1 ml (5.55 mMol) of $^3$H$_2$O (specific radioactivity 3 mCi/mMol) are added to 414.5 mg (1 mMol) IIb which is dissolved in 3 ml THF. 20 mg lithium methylate are added at room temperature after 10 mins., and the reaction is allowed to proceed for 15 min. when it is terminated by the addition of 0.5 ml of glacial acetic acid. Concentration is made thereafter and the residue is mixed with 4 ml abs. of Pyridin and 4 ml of acetic anhydride. This is again concentrated after 20 mins. and the residue is chromatographed on 30 g silica gel (Woelm). Elution with chloroform/n-hexane 6:4 vol/vol, will yield 265 mg ≙ 64% of the theoretical amount of [15-$^3$H]-O(3),O(13)-diacetylgibberellin-A$_3$-(7)-aldehyde(IIc) with a specific radioactivity of 1.34 mCi/mMol; mp: 161°–163° C. (from ether/n-hexane); $[d]_D^{25}$ +205.5° (c=0.51, abs. dioxane); IR (CHCl$_3$): $\nu_{max}$ 2820, 2725 and 1725 (aldehyde) 1775 ($\gamma$-lactone-CO), 1740 (ester-CO), 1665 (>C=CH$_2$) and 1255 cm (acetate); MS: m/e 414 (M+).

The analogous reaction of 414.5 mg of IIb in 3 ml of THF with 0.1 ml of $^2$H$_2$O (99.9% purity) and 20 mg of lithium methylate will yield after acetylization 257 mg=62% of the theoretical value /15-$^2$H/-O(3),O(13)-diacetylgibberellin-A$_3$-(7)-aldehyde (X): m.p. 160°–164° C. (from ether/n-hexane); $[d]_D^{25}$+204.1° (c=0.46 abs. dioxane): MS: m/e 415 (M+). Deacetylization of 143 mg X with 3.5 ml of 0.2 n sodium methylate in solution (4 hours at room temperature) will yield after chromatographic treatment 78 mg ≙ 68% of the theor. value of [15-$^2$H]-gibberellin-A$_3$-(7)-aldehyde: amorph. $[d]_D^{25}$+119.0° (c=0.60, ethanol); MS: m/e 331 (M+).

EXAMPLE 3

A solution of 414.5 mg (1 mMol) of O(3),O(13)-diacetyl-gibberellin-A$_3$-(7)-aldehyde(IIa) in 60 ml of chloroform is concentrated under vacuum in a quartz flask. The substance remaining as a film, is placed under an argon blanket, rotated, and irradiated with ultraviolet light (cooling by hair-drier-type blower; THU 500 of Messrs. THELTA Electro Apparatus, Zella-Mehlis) for 70 hours. The photo product obtained is then chromatographed on 30 mg silica gel (Woelm). The fractions 22–27 with a gradient of n-hexane/chloroform 3:7 vol/vol will return a yield of 120 mg O(3), O(13)-diacetylgibberellin-A$_3$-(7)-aldehyde(IIa). The same gradient will yield on combination of the fractions 30–55, 236 mg ≙ 80% of the theoretical value of ent-3α, 13-diacetoxy-7ε, 10-dihydroxy-7, 15-cyclo-20-norgibberellan-1, 16-diene-19-acid-19,10-lactone(IIb) (Yield relative to converted IIa).

4 ml of acetic anhydride are added to 414.5 mg ent-3α, 13-diacetoxy-7, 10-dihydroxy-7, 15-cyclo-20-norgibberella-1, 16-diene-19-acid-19, 10-lactone in 4 ml of pyridine. After allowing to stand for one hour at room temperature, concentration is made under vacuum. The residue is chromatographed on 30 mg of silica gel. With n-hexane/chloroform 6:4 vol/vol, this will yield 389 mg ≙ 85% of the theoretical value of ent-3d, 7, 13-triacetoxy-10-hydroxy-7, 15-cyclo-20-norgibberella-1, 16-diene-19, 10-lactone: mp. 229°–231° C. (from ether), $[d]_D^{25}$+158.0 (c=0.63, ethanol); MS m/e 456 (M+); IR (CHCl$_3$): $\nu_{max}$ 1778 ($\gamma$-lactone-CO), 1740 (ester-CO), 1670 (C=CH$_2$) and 1260 cm$^{-1}$ (acetyl).

To 228 mg (0.5 mMol) ent-3α, 7β, 13-triacetoxy-10-hydroxy-7-15-cyclo-20-norgibberella-1, 16-diene-19-acid-19, 10-lactone add 5 ml abs. of THF and 0.05 ml $^3$H$_2$O (spec. radioactivity=3 mCi/mMol). During one hour, 112.2 mg (1 mMol) of alcohol-free potassium tert butylate are added in portions, stirred for one further hour, and 0.3 ml of glacial acetic acid are then added. After concentration under vacuum and addition of 2 ml of pydridin and 2 ml of acetic anhydride, this will yield, after concluding treatment, (vide example 2) 153 mg ≙ 67% of theoretical value, of [15-$^3$H]-O(3),O(13)-diacetyl-gibberellin-A$_3$-(7)-aldehyde(IIc), (spec. radioactivity=1.5 mCi/mMol).

Deacetylating of 153 mg of IIc with 3.7 ml of a solution of 0.2 n sodium methylate will, corresponding to example 1, yield after chromatography 85 mg ≙ 70% of the theoretical value of [15-$^3$H]-gibberellin-A$_3$-(7)-aldehyde(Ic) (spec. radioactivity=1.48 mCi/mMol).

EXAMPLE 4

A solution of 41.5 mg (0.1 mMol) of O(3),O(13)-diacetyl-gibberellin-A$_3$-(7)-aldehyde(IIa) in 2 ml abs. of THF is combined with 0.05 ml of $^3$H$_2$O (spec.radioactivity=3 mCi/mMol) and irradiated for 80 hours with ultraviolet light in a Pyrex flask (hair-drier-type blower f. cooling; THU 500 of Messrs. THELTA Electro Apparatus, Zella-Mehlis). After concentration under vacuum, absorption by ether and multiple shaking-out with water follow. The residue of the dried and concentrated ether phase is chromatographed on 2 g of silica gel (Woelm). Under the same conditions of elution as in example 2, a yield is obtained of 17.4 mg ≙ 42% of the theor. amount of [15-$^3$H]-O(3),O(13)-diacetyl gibberellin-A$_3$-(7)-aldehyde(IIc) (spec. radioactivity=0.11 mCi/mMol) and 20.7 mg ≙ 50% of the theory, ent-3α, 13-diacetoxy-7ξ, 10-dihydroxy-7, 15-cyclo-20-norgibberella-1, 16-diene-19-acid-19, 10-lactone(IIb).

EXAMPLE 5

374.5 g (1 mMol) O(3)-acetyl gibberellin-A$_1$-(7)-aldehyde(IIIa) in a quartz flask under nitrogen, are irradiated at 25° C. for 26 hours (THU 500 of Messrs. THELTA Electro Apparatus, Zella-Mehlis). After concentration under vacuum, the residue is chromatographed on 25 g silica gel (Woelm). With n-hexane/chloroform, 2:8 vol/vol, a yield is returned of 63 mg O(3)-acetylgibberellin-A$_1$-(7)-aldehyde. Subsequent elution with chloroform yields 271 mg ≙ 87% of the isomer mixture ent-3α-acetoxy-7ξ, 10, 13-trihydroxy-7, 15-cyclo-20-norgibberella-16-en-19-acid-19, 10-lactone (IIIb): IR (CHCl$_3$): $\nu_{max}$ 3610 (OH), 1780 ($\gamma$-lactone-CO), 1740 (ester-CO), 1665 (>C=CH$_2$) and 1260 cm$^{-1}$ (acetyl); MS: m/e 374 (M+).

To 271 mg IIIb, dissolved in 2 ml methanol, 0.5 ml $^3$H$_2$O (spec. radioactivity=3 mCi/mMol) and 150 mg water-free sodium acetate are added and the mixture left standing at room temperature for 1½ weeks. The mixture is then concentrated, ether is added and the ether phase is shaken out with water repeatedly.

Drying of the ether solution with sodium sulfate and concentration in vacuum, yield a substance which is combined with 4 ml pyridin and 4 ml acetic anhydride. After 10 minutes, concentration in vacuum is repeated, and the residue chromatographed on 20 g silica gel. with n-hexane/chloroform 2:8 vol/vol, a yield is obtained of 184 mg ≙ 68% of the theor. value, amorphous/15-$^3$H/-O(3)-acetyl gibberellin-A$_1$-(7)-aldehyde(IIIc): IR(CHCl$_3$): $\nu_{max}$ 3610 (OH), 2725, 2820 and 1725 (aldehyde), 1775 ($\gamma$-lactone-CO), 1740 (ester-CO), 1665 (>C=CH$_2$), 1255 cm$^{-1}$ (acetate); MS: m/e 374 (M$^{+f.i.}$M$^-$). The specific radioactivity amounts to 0.23 mCi/mMol.

Deacetylation of 153 mg IIIc with 2 ml of a solution of 0.2 n sodium methylate will yield, after chromatography, 99 mg ≙ 73% of the theor. value [15-$^3$H]-gibberellin-A$_1$-(7)-aldehyde: amorph; $[\alpha]_D^{25}$ +62.8° (c=0.42, ethanol); MS: m/e 332 (M$^+$). The specific radioactivity amounts to 0.20 mCi/mMol.

EXAMPLE 6

35.8 mg (0.1 mMol) O(3)-acetyl gibberellin-A$_4$-(7)-aldehyde(IVa) in 5 ml methylene chloride in a quartz flask under argon, are irradiated for 25 hours by a high pressure mercury burner (THU 500 of Messrs. THELTA Electro Apparatus Zella-Mehlis). During the photochemical reaction, temperature is maintained between minus 30° C. and minus 60° C. Therafter, the solution is concentrated in a vacuum and the resideu chromatographed on 2.5 g silica gel (Woelm). Elution with n-hexane/chloroform 4:6 vol/vol yields 7.2 mg unconverted O(3)-acetyl gibberellin-A$_4$-(7)-aldehyde(IVa). With n-hexane/chloroform 3:7 vol/vol, a yield is obtained of 17.5 mg ≙ 61% of the theoretical value (relative to converted IVa) ent-3$\alpha$-acetoxy-7$\xi$, 10-dihydroxy-7, 15-cyclo-20-norgibberella-16-en-19-acid-19, 10-lactone(IVb): MS: m/e 358 (M$^+$); IR (CHCl$_3$): $\nu_{max}$ 3610 (OH), 1780 ($\gamma$-lactone-CO), 1740 (ester-CO) and 1260 cm$^{-1}$ (acetyl).

17.9 mg of IVb (0.05 mMol) are added to a tritiated solution of sodium phenolate [prepared from 1 g C$_6$H$_5$O-$^3$H (spec. radioactivity=12 $\mu$Ci/mMol) and 3 mg Na], that has been heated to 50° C. The reaction is terminated after three hours by the addition of 0.2 ml glacial acetic acid. Subsequent double chromatography on 2.5 mg silica gel is required to separate phenol from gibberellin. Elution with n-hexane/chloroform 2:8 vol/vol will yield 8.6 mg ≙ 54% of the theor. value, amorphous [15-$^3$H]-gibberellin-A$_4$-(7)-aldehyde: IR (CHCl$_3$): $\nu_{max}$ 3610 (OH), 2725, 2820 and 1725 (aldehyde) and 1775 cm$^{-1}$ ($\gamma$-lactone-CO); MS: m/e 316 (M$^+$). The specific radioactivity amounts to 10 $\mu$Ci/mMol.

EXAMPLE 7

314.4 mg (1 mMol) gibberellin-A$_5$-(7)-aldehyde(Va) are dissolved in 50 ml tert. butanol and then irradiated in a quartz flask for 20 hours with UV light (THU 500 of Messrs. THELTA Electro Apparatus) at 30° C.-50° C. After concentration in vacuum, the residue is chromatographed on 25 g silica gel. Elution with n-hexane/chloroform 1:9 vol/vol yields 40 mg gibberellin-A$_5$-(7)-aldehyde(Va). Subsequent elution with chloroform yields 195 mg ≙ 71% of the theor. value ent-7$\xi$, 10, 13-trihydroxy-7, 15-cyclo-20-norgibberella-2, 16-diene-19-acid-19,10-lactone(Vb) (calculation of yield relative to converted Va): IR(CHCl$_3$): $\nu_{max}$ 3600-3610 (OH), 1770 ($\gamma$-lactone-CO) and 1660 cm$^{-1}$ (>C=CH$_2$); MS: m/e 314 (M$^+$).

195 mg Vb in 20 ml abs. THF are metalated in 20 ml abs. THF under Argon at −78° C. with two equivalents lithium diisopropylamide (from diisopropylamine and butyllithium). 1 ml $^3$H$_2$O (spec. radioactivity=3 mCi/mMol) are then added and the mixture allowed to warm up to room temperature. The reaction is terminated by the addition of 1 ml glacial acetic acid. The mixture is subsequently concentrated, combined with ether, the etheric solution repeatedly shaken out with water, dried, concentrated and the residue chromatographed on 15 g silica gel (Woelm). Elution with n-hexane/chloroform 1:9 vol/vol yields 123 mg ≙ 63% of the theor. amount [15-$^3$H]-gibberellin-A$_5$-(7)-aldehyde(Vc): IR (CHCl$_3$): $\nu_{max}$ 3600 (OH), 2725, 2820 and 1725 (aldehyde) and 1775 ($\gamma$-lactone-CO); MS: m/e 314 (M$^+$). The specific radioactivity of Vc amounts to 1.4 mCi/mMol.

EXAMPLE 8

31.4 mg (0.1 mMol) gibberellin-A$_7$-(7)-aldehyde (VIa) in crystalline form without a solvent, are irradiated per 80 hours with UV light (THU 500 of Messrs. THELTA Electro Apparatus) in a quartz flask, with cooling by a hair-drier-type blower. The mixed substance is then chromatographed on 1.5 g silica gel (Woelm) with n-hexane/chloroform 1:9 vol/vol, 3.6 mg unconverted VI a are obtained. Elution with chloroform yields 17 mg ≙ 61% of the theor. value amorph. ent-3$\alpha$, 7$\xi$, 10-trihydroxy-7, 15-cyclo-20-norgibberella-1, 16-diene-19-acid-19, 10-lactone(VIb), (yield calculation relative to converted VIa): IR (CHCl$_3$): $\nu_{max}$ 3610 (OH), 1775 ($\gamma$-lactone-CO) and 1660 cm$^{-1}$ (>C=CH$_2$); MS: m/e 314 (M$^+$). 17 mg VIb are dissolved in 2 ml methanol and combined with 0.1 ml $^3$H$_2$O (spec. radioactivity of $^3$H$_2$O=3 mCi/mMol). This mixture is obtained by anion exchangers (Dowex, OH-form). Chromatography on 1 g silica gel (Woelm) of the residue obtained after concentration yields with n-hexane/chloroform 1:9 vol/vol, 8.8 mg ≙ 52% of the theor. value [15-$^3$H]- gibberellin-A$_7$-(7)-aldehyde(VIc): m.p.: 183°-187° C.; IR (CHCl$_3$): $\nu_{max}$ 3610 (OH), 2720, 2820 and 1725 (aldehyde), 1775 ($\gamma$-lactone-CO) and 1665 cm$^{-1}$ (>C=CH$_2$); MS: m/e 314 (M$^+$). The specific radioactivity of Vic amounts to 20 $\mu$Ci/mMol.

EXAMPLE 9

A solution of 34.8 g (0.1 mMol) gibberellin-A$_8$-(7)-aldehyde(VIIa) in 6 ml THF in a Pyrex flask, is irradiated with UV light (THU 500 of Messrs. THELTA Electro Apparatus) for 60 hours. Concentration in vacuum is made thereafter and the residue chromatographed on 4 g silica gel (Woelm). With a gradient of chloroform/methyl acetate of 4:6 vol/vol, 16.2 mg of converted gibberellin-A$_8$-(7)-aldehyde are obtained. Further elution with chloroform/ethyl acetate 2:8 vol/vol yields 15.3 mg ≙ 82% of the theor. value amorphous ent-2$\alpha$, 3$\alpha$, 7$\xi$-10, 13-pentahydroxy-7, 15-cyclo-20-norgibberella-1, 16-diene-19-acid-19, 10-lactone (VIIb) (Yield calculated relative to converted VIIa): IR (Nujol): $\nu_{max}$ 3400 br. (OH) and 1755 cm$^{-1}$ ($\gamma$-lactone-CO); MS: m/e 348 (M$^+$).

15 mg VIIb are combined with or tritiated solution of lithium-n-propylmercaptid [prepared from 1 ml n-

$C_3H_7S$-$^3H$ (specific radioactivity 43 μCi/mMol) and 0.1 ml butyllithium in n-hexane (content 3.2 mg $C_4H_9Li$)]. After one hour, 0.1 ml glacial acetic acid are added and concentration in vacuum performed. Subsequent chromatography on 1 g silica gel (Woelm) will yield, with chloroform/ethyl acetate 4:6 vol/vol, 8.1 mg ≙ 54% of the theoretical amount amorphous [15-$^3H$]-gibberellin-$A_8$-(7)-aldehyde(VIIc) (spec. radioactivify 30 μCi/mMol): IR (Nujol): $\nu_{max}$ 3400 br. (OH), 1755 (γ-lactone-CO) and 1720 cm$^{-1}$ (aldehyde); MS: m/e 348 (M+).

EXAMPLE 10

To 3 mg (0.01 mMol) gibberellin-$A_9$-(7)-aldehyde(VIIIa), dissolved in 1 ml tritiated tert. butanol (spec. radioactivity of $C_4H_9O$-$^3H$ = 34 μCi/mMol), in a quartz flask, 3 mg potassium tert. butylate are added. The solution is then irradiated with ultraviolet light (THU 500 of Messrs. THELTA Electro Apparatus) for 23 hours, with cooling by a hair-drier-type blower. 0.1 ml glacial acetic acid is then added and concentration in vacuum performed. Subsequent chromatography on 0.5 mg silica gel (Woelm) yields, with n-hexane/chloroform 1:1 vol/vol, 1.7 mg ≙ 57% of the theor. value, amorphous [15-$^3H$]-gibberellin-$A_9$-(7)-aldehyde(VIIIc) (spec. radioactivity=28 μCi/mMol): IR (CHCl$_3$): $\nu_{max}$ 2820, 2725 and 1725 (aldehyde) and 1775 cm$^{-1}$ (γ-lactone-CO); MS: m/e 300 (M+).

EXAMPLE 11

A solution of 3.2 mg (0.01 mMol) of gibberellin-$A_{12}$-(7)-aldehyde(IXa) in 1 ml ethyl acetate in a quartz flask under argon, is irradiated for 32 hours by a high-pressure mercury burner (THU 500 of Messrs. THELTA Electro Apparatus, Zella-Mehlis) under cooling by hair-drier-type blower. Concentration in vacuum is performed subsequently and after thin-layer chromatography on silica gel (Merck) a yield is obtained of 0.7 mg gibberellin-$A_{12}$-(7)-aldehyde (IXa) and 2.2 mg ≙ 88% of the theor. value of ent-7ξ-Hydroxy-7, 15-cyclo-gibberella-16-en-19-acid(IXb) (yield calculation relative to converted IXa): MS: m/e 316 (M+).

To 2.2 mg of IXb add 0.1 ml of a tritiated sodium methylate solution (prepared from $CH_3O$-$^3H$, spec. radioactivity 37 μCi/mMol and 1 mg Na). After 20 minutes, the reaction is terminated by the addition of 0.1 ml glacial acetic acid and concentration in vacuum is made thereafter. Subsequent thin-layer chromatography on silica gel (Merck) will yield 1.3 mg ≙ 59% of the theoretical value of [15-$^3H$]-gibberellin-$A_{12}$-(7)-aldehyde(IXc) (spec. radioactivity 35 Ci/mMol); IR (CHCl$_3$): $\nu_{max}$ 2725 (CHO), 1710 br. (>C=O) and 1658 cm$^{-1}$ (>C=CH$_2$); MS: m/e 316 (M+).

We claim:
1. [15-$^2H$]-gibberellin-(7)-aldehydes.
2. [15-$^3H$]-gibberellin-(7)-aldehydes.
3. [15-$^3H$]-gibberellin-$A_1$-(7)-aldehyde.
4. [15-$^3H$]-gibberellin-$A_3$-(7)-aldehyde.
5. [15-$^3H$]-gibberellin-$A_4$-(7)-aldehyde.
6. [15-$^3H$]-gibberellin-$A_5$-(7)-aldehyde.
7. [15-$^3H$]-gibberrellin-$A_7$-(7)-aldehyde.
8. [15-$^3H$]-gibberellin-$A_8$-(7)-aldehyde.
9. [15-$^3H$]-gibberellin-$A_9$-(7)-aldehyde.
10. [15-$^3H$]-gibberellin-$A_{12}$-(7)-aldehyde.
11. [15-$^3H$]-O(3)-Acetylgibberellin-$A_1$-(7)-aldehyde.
12. [15-$^2H$]-O(3),O(13)-Diacetylgibberellin-$A_3$-(7)-aldehyde.
13. [15-$^3H$]-O(3),O(13)-Diacetylgibberellin-$A_3$-(7)-aldehyde.

* * * * *